United States Patent [19]

Ornstein

[11] Patent Number: 4,902,687

[45] Date of Patent: Feb. 20, 1990

[54] EXCITATORY AMINO ACID RECEPTOR ANTAGONISTS

[75] Inventor: Paul L. Ornstein, Indianapolis, Ind.

[73] Assignee: Eli Lilly and Company, Indianapolis, Ind.

[21] Appl. No.: 328,848

[22] Filed: Mar. 27, 1989

[51] Int. Cl.[4] .................. A61K 31/495; C07D 403/06; C07D 403/14

[52] U.S. Cl. ...................................... 514/253; 544/366

[58] Field of Search ................................ 544/366, 253

[56] References Cited

U.S. PATENT DOCUMENTS

| | | | |
|---|---|---|---|
| 3,536,715 | 10/1970 | Hayao et al. | 260/268 |
| 4,746,653 | 5/1988 | Hutchinson et al. | 514/87 |
| 4,761,405 | 8/1988 | Rzeszotarski et al. | 514/114 |

FOREIGN PATENT DOCUMENTS 159889 10/1985 European Pat. Off. .

OTHER PUBLICATIONS

Derwent, 88-198230/29 Abstracting AU 8781-455.

*Primary Examiner*—Mukund J. Shah
*Assistant Examiner*—Cecilia Shen
*Attorney, Agent, or Firm*—Robert A. Conrad; Leroy Whitaker

[57] ABSTRACT

The present invention provides novel piperazine derivatives useful as excitatory amino acid receptor antagonists and in treating a variety of associated nervous system disorders.

18 Claims, No Drawings

EXCITATORY AMINO ACID RECEPTOR ANTAGONISTS

SUMMARY OF THE INVENTION

The present invention provides compounds which are antagonists of excitatory amino acid receptors. More specifically, the present invention relates to piperazine compounds of the formula

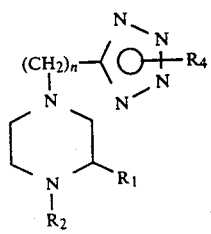

wherein:
$R_1$ is

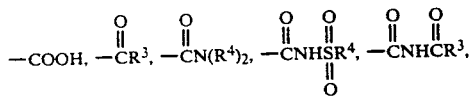

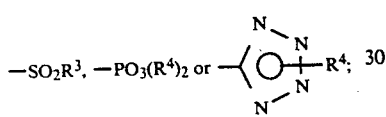

$R_2$ is hydrogen, $C_1-C_4$ alkyl; or phenyl-substituted $C_1-C_4$ alkyl;

n is 2 or 3;

each $R^3$ is independently $C_1-C_{16}$ alkoxy, phenyl-substituted $C_1-C_4$ alkoxy, or an oral ester forming group;

each $R^4$ is independently hydrogen, $C_1-C_{16}$ alkyl, phenyl-substituted $C_1-C_4$ alkyl, or phenyl; or a pharmaceutically acceptable salt thereof.

The invention also provides pharmaceutical formulations comprising a compound of Formula I and a pharmaceutically acceptable carrier, diluent or excipient therefor.

Further embodiments of the invention include a method of blocking one or more excitatory amino acid receptors, as well as methods for treating a variety of disorders which have been linked to the excitatory amino acid receptors including neurological disorders (for example, epilepsy), stroke, anxiety, cerebral ischaemia, muscular spasms and neurodegenerative disorders such as Alzheimer's Disease and Huntington's Disease, employing a compound of Formula 1.

DETAILED DESCRIPTION OF THE INVENTION

In the above formula, the term "$C_1-C_{16}$ alkyl" represents a straight or branched alkyl chain having from one to sixteen carbon atoms. Typical $C_1-C_{16}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, undecyl, hexadecyl, and the like. The term "$C_1-C_{16}$ alkyl" includes within it the terms "$C_1-C_6$ alkyl" and "$C_1-C_4$ alkyl". The term "$C_1-C_{16}$ alkoxy" can be represented by ($C_1-C_{16}$ alkyl)-O- and includes within it the term "$C_1-C_4$ alkoxy".

The term "phenyl-substituted $C_1-C_4$ alkyl" represents a $C_1C_4$ alkyl group bearing a phenyl group, such as benzyl, 1-phenylethyl, 2-phenylethyl, 3-phenylpropyl, 4-phenylbutyl, 2-methyl-2-phenylpropyl, and the like.

The term "oral ester forming group," as used herein, represents a substituent which, when attached to the carboxylic acid group, forms an ester function suitable for administration to mammals in need of treatment. Examples of such oral ester forming groups include $C_1-C_4$ alkoxy; benzyloxy; benzyloxy substituted on the phenyl ring with halogen, $C_1-C_4$ alkyl or $C_1-C_4$ alkoxy; $C_4-C_7$ alkanoyloxymethyl; or $C_4C_7$ alkanoyloxymethyl substituted on the oxomethyl with $C_4-C_7$ alkyl or $C_4-C_7$ cycloalkyl.

While all the compounds of the present invention are believed to be antagonists of excitatory amino acid receptors, there are certain compounds of the invention which are preferred for such use. Preferably, $R_1$ is —COOH, the $R^4$ substituted on the tetrazole ring is hydrogen, and $R_2$ is hydrogen, i.e., the compounds of Formula Ia.

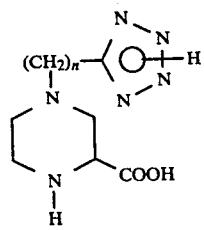

The compounds of the present invention possess an asymmetric carbon atom represented by the carbon atom substituted by $R_1$. As such, the compounds can exist as a racemic mixture of isomers or each individual optical isomer. Accordingly, the compounds of the present invention will include not only the racemates, but also their respective optically active isomers.

As pointed out above, this invention includes the pharmaceutically acceptable salts of the compounds defined by Formula I. These salts can exist in conjunction with the acidic or basic portion of the molecule and can exist as acid addition, primary, secondary, tertiary or quaternary ammonium or alkali metal or alkali earth metal salts. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, metaphosphate, pyrophosphate, chloride, lithium bromide, iodide, acetate, magnesium, propionate, tetramethylammonium, decanoate, caprylate, acrylate, formate, isobutyrate, caprate, heptanoate, potassium, propiolate, oxalate, trimethylammonium, malonate, succinate, suberate, sebacate, fumarate, maleate, butyne-1,4-dioate, sodium, hexyne-1,6-dioate, benzoate, chlorobenzoate, methylbenzoate, dinitrobenzoate, hydroxybenzoate, methoxybenzoate, phthalate, sulfonate, methylammonium, xylenesulfonate, phenylacetate, phenylpropionate, phenylbutyrate, citrate, lactate, calcium, β-hydroxybutyrate, glycollate, maleate, tartrate, methanesulfonate, propanesulfonate, naphthalene-1-sulfonate, naphthalene-2-sulfonate, mandelate and the like salts.

Compounds of the present invention can contain one or two tetrazole rings. Tetrazole is known to exist as tautomeric structures. The tetrazole having the double bond on the nitrogen atom at the 1-position and the R substituent on the N-2 nitrogen atom is properly named as a 2H-tetrazole and is represented by the following structure:

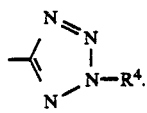

This compound has a corresponding tautomeric form wherein the R substituent is at N-1 with the double bond on the nitrogen atom of the 4-position. These compounds are named in part as 1H-tetrazoles and possess the following part structure:

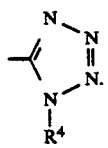

Mixtures of the two tautomers are referred to herein as 1(2)H-tetrazoles. The present invention contemplates both individual tautomeric forms as well as the combination of the two tautomers.

The compounds of the present invention may be prepared by procedures well known to those of ordinary skill in the art. To prepare the preferred carboxylic acid derivatives of Formula Ia, a substituted pyrazine is converted into the fully saturated piperazine. The nitrogen atom adjacent to the prospective $R_1$ substituent is blocked with a standard blocking reagent after the other nitrogen atom is alkylated with an omega-halo alkylnitrile. The nitrile group is then transformed into a tetrazole group, the other nitrogen atom is deblocked, and the $R_1$ precursor hydrolyzed to provide the carboxylic acid of Formula Ia. Scheme I is illustrative of this conversion.

Scheme I

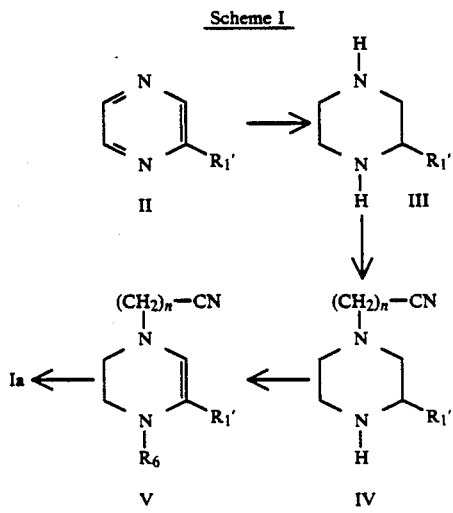

wherein:
$R^{1'}$ is —CONH$_2$ or —COO(C$_1$-C$_4$ alkyl) and R$_6$ is C$_1$-C$_6$ alkoxycarbonyl.

According to Scheme I, pyrazine II is reduced to afford the corresponding piperazine III. This reaction is best accomplished by standard hydrogenation procedures in the presence of a catalyst, such as platinum oxide, in a nonreactive solvent such as an alcohol, particularly ethanol, preferably in the presence of acetic acid.

Intermediate III is then alkylated with a suitable ω-haloalkyl nitrile in the presence of a base, such as Hunig's base, to provide the corresponding cyanoalkyl intermediate IV. This intermediate is then protected with a blocking group preferably a C$_1$-C$_6$ alkoxycarbonyl group, to provide the protected intermediate V.

This cyano derivative is then converted to a tetrazole intermediate and then to the compound of the invention according to the following process. The cyano starting material is reacted with tributyltin azide (also known as azido tributylstannane). This reaction is conducted at a temperature of about 50° C. to about 120° C., preferably at about 80° C., for about 12 to about 120 hours. The product may be isolated, but is preferably hydrolyzed directly to a compound of the invention by standard acid or base hydrolysis. The reaction is conducted at a temperature in the range of about 50° C. to about 150° C. for about 2 hours to about 24 hours and the product isolated. The product may then be purified by standard procedures such as crystallization with common solvents such as water, acetone or ethanol, or chromatography over solid supports such as silica gel, ion exchange resins or standard absorbents. This reaction, when followed by acidic workup, not only effectively converts the nitrile intermediate to the desired tetrazole, but is also effective for removing the blocking group R$_6$ and hydrolyzes the $R_1'$ group into a carboxylic acid.

Compounds of the invention wherein $R_1$ is other than the free carboxylic acid substituent are prepared by procedures well known to one of ordinary skill in the art. Compounds wherein $R_1$ is —C(=O)R$^3$ and R$^3$ is C$_1$-C$_{16}$ alkoxy or phenyl substituted C$_1$-C$_4$ alkoxy are prepared by esterification of the free carboxylic acid with an appropriate alcohol R$^3$H in the presence of hydrogen chloride gas. The compounds wherein R$^1$ is —C(=O)R$^3$ and R$^3$ is an oral ester forming group are prepared by standard alkylation or acylation techniques. Compounds wherein $R_1$ is —C(=O)O(phenyl), —C(=O)N(R$^4$)$_2$, —C(=O)NHSO$_2$R$^4$ or —C(=O)NHC(=O)R$^3$ are prepared by the reaction of the free carboxylic acid derivative of the intermediate which is blocked with R$_6$ as defined above (either isolated as a partial hydrolysis product in the conversion of V to I or Ia which has been converted into a N-R$_6$ blocked intermediate in the same manner as described above) with an appropriately substituted amine NH(R$^4$)$_2$, sulfonamine NH$_2$SO$_2$R$^4$ or acylamine NH$_2$C(=O)R$^3$ in the presence of a coupling reagent and mutual organic solvent. Suitable coupling reagents include the carbodiimides such as N,N'-dicyclohexylcarbodiimide, N,N'-diisopropylcarbodiimide, or N,N'-diethylcarbodiimide; the imidazoles such as carbonyldiimiaazole; as well as reagents such as N-ethoxycarbonyl-2-ethoxy-1,2-dihydroquinoline (EEDQ). The resulting compound is then deblocked of the R$_6$ group as hereinbefore described. Compounds wherein $R_1$ is tetrazole or substituted tetrazole can also be prepared by treating the carboxylic acid Ia with ammonia in the presence of a coupling reagent as described above to provide the corresponding primary carboxamide. The carboxamide is dehydrated to the corresponding carbonitrile upon treatment with phenylphosphinoyl dichloride or triphenylphosphine dibromide, in the presence of a tertiary amine such as triethylamine or pyridine. The resulting compound is converted to the tetrazole intermediate with tributyltin azide according to conditions hereinbefore described. The desired compound is then prepared as hereinbefore described.

Compounds of the present invention wherein the $R^4$ substituent on the tetrazole ring is other than hydrogen may also be prepared by known processes, or by processes analogous to such known procedures. Typically, alkylation of the unsubstituted starting material with an appropriate halide reagent $R^4$-Cl, $R^4$-Br, or $R^4$-I provides the desired compound of the invention or an intermediate which can be further modified to a compound of the invention as herein described. If a base is employed in the alkylation reaction, addition occurs first on the tetrazole ring if the other free nitrogen atoms are unsubstituted. Conducting the reaction in tho absence of a base leads to preferential addition on the piperidine nitrogen atom. Any free nitrogen atom may also be blocked prior to the reaction, and deblocked subsequently according to standard conditions employing standard blocking reagents. Of course, di-substitution with the same substituent merely requires the use of two appropriate molar equivalents of reagent to account for each of the desired substituents on the final compound. As will be appreciated by those skilled in organic synthesis, the particular pattern of substitution, in the case where $R_1$ is tetrazolyl, can be controlled by the use of blocking agents or introducing and functionalizing one tetrazolyl group before the other tetrazolyl group is introduced.

The pharmaceutically acceptable salts of the invention are typically formed by reacting a compound of this invention with an equimolar or excess amount of salt forming reagent. The reactants are generally combined in a mutual solvent such as diethyl ether, benzene, ethanol or water and the salt normally precipitates out of solution within about one hour to 10 days, and can be isolated by filtration.

The pyrazine intermediates corresponding to Formula II employed as starting materials in the synthesis of the compounds of this invention are known or can be prepared by procedures well known to those of ordinary skill in the art.

The following Examples further illustrate the compounds of the present invention and methods for their synthesis. The Examples are not intended to be limiting to the scope of the invention in any respect and should not be so construed.

EXAMPLE 1

4-[3-(1(2)H-tetrazol-5-yl)propyl]-2-piperazinecarboxylic acid

A. Preparation of 2-piperazinecarboxamide diacetate (salt).

One hundred twenty-five grams of pyrazinamide were hydrogenated in the presence of 2.5 L of 6:1 ethanol/acetic acid and 62.6 g of platinum oxide at 60 psi and 60° C. After hydrogen uptake ceased, the reaction mixture was filtered through a Celite ® pad and concentrated in vacuo. Trituration with ethyl acetate afforded 219.57 g of the desired subtitle intermediate, m.p. 90–92° C.

B. Preparation of 4-(3-cyanopropyl)-1-t-butoxycarbonyl-2-piperazinecarboxamide.

Eighty grams of the amide from Example 1A above were mixed with 300 ml of ethanol and 124.4 g of Hunig's base. With stirring, 49 g of 4-bromobutyronitrile were added. The mixture was heated at 85° C. overnight under a nitrogen atomosphere. An additional 8.2 ml of 4-bromobutyronitrile were added and the solution heated at reflux for 6 hours more. The reaction was cooled to room temperature and portions of di-t-butyl dicarbonate totalling 147.4 ml were added over a 15 minute period. After stirring for 30 minutes at room temperature, the mixture was concentrated in vacuo. The residue was taken up in ethyl acetate and filtered. The filtrate was concentrated in vacuo and the residue purified by high pressure liquid chromatography over silica gel. The appropriate fractions were combined and concentrated in vacuo to provide 44.63 g of the desired subtitle intermediate as an oil.

C. Preparation of 4-[3-(1(2)H-tetrazol-5-yl)propyl]-2-piperazinecarboxylic acid.

The nitrile from Example 1B above (43.76 g) was treated with 98.1 g of tributyl tin azide and then heated for 4 days at 80° C. under a nitrogen atmosphere. After cooling to room temperature, 450 ml of methanol, previously saturated with hydrogen chloride gas, were added. After stirring for 2 hours, the mixture was concentrated in vacuo. The residue was dissolved in 400 ml of water and the mixture was extracted three times each with 350 ml of diethyl ether. The aqueous layer was concentrated in vacuo, treated with 350 ml of 6 N hydrochloric acid, and heated at reflux overnight. One hundred milliliters of water were added and the mixture concentrated in vacuo. The residue was treated with acetone (18 hours at room temperature and 1 hour at reflux). The acetone was decanted and the residue concentrated in vacuo. The residue was dissolved in 75 ml of water and purified by ion-exchange chromatography over Dowex 50X8 resin. The appropriate fractions were combined and concentrated in vacuo. The residue was suspended in acetone and refluxed for 1 hour. After cooling, the material was filtered and washed with acetone and diethyl ether, providing 22.03 g of the desired title product, m.p. =153–156° C.

Analysis for $C_9H_{16}N_6O_2$:

Calc.: C, 44.99; H, 6.71; N, 34.98;
Found: C, 44.70; H, 6.80; N, 34.72.

EXAMPLE 2

4-[2-(1(2)H-tetrazol-5-yl)ethyl]-2-piperazinecarboxylic acid.

Following the procedure of Examples 1B and 1C above, the piperazine amide and 3-bromopropionitrile were reacted to provide the corresponding 4-(2-cyanoethyl)-1-t-butoxycarbonyl-2-piperazinecarboxamide intermediate in 30% yield, m.p. 117–118° C. This nitrile was then transformed into the desired title product except that the final hydrolysis was done in 3:1 methanol:2N sodium hydroxide at reflux overnight. After cooling and concentration in vacuo, the product was acidified with 1N hydrochloric acid, then concentrated in vacuo. Purification as in Example 1B afforded the product in 73% yield, m.p. 220–224° C.

Analysis for $C_8H_{14}N_6O_2 \cdot 0.7\ H_2O \cdot 0.1\ C_3H_6O$ (acetone):
Calc.: C, 40.91; H, 6.65; N, 34.12;
Found: C, 40.75; H, 6.59; N, 34.35.

As noted above, the compounds of this invention are excitatory amino acid antagonists. Therefore, another embodiment of the present invention is a method of blocking one or more excitatory amino acid receptors in mammals which comprises administering to a mammal requiring decreased excitatory amino acid neurotransmission a pharmaceutically effective amount of a compound of the invention.

The term "pharmaceutically effective amount", as used herein, represents an amount of a compound of the invention which is capable of blocking one or more excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by excessive stimulation of excitatory amino acid neurotransmission. As such, the compounds of the present invention are believed to have the ability to treat a variety of disorders in mammals associated with this condition which include neurological disorders such as convulsive disorders for example, epilepsy; stroke; anxiety; cerebral ischaemia; muscular spasms; and neurodegenerative disorders such as Alzheimer's Disease and Huntington's Disease. Therefore, the present invention also provides methods of treating the above disorders at rates set forth above for excitatory amino acid receptors in mammals.

Experiments were performed to demonstrate inhibitory activity of compounds of this invention at the N-methyl-D-aspartate (NMDA) subtype of excitatory amino acid receptor in the rat in vivo.

Male or female neonatal (7 to 8 days old) Sprague-Dawley rats were removed from the dam and placed in plastic observation chambers that were maintained at 30–32° C. All test drugs were dissolved in normal saline. Activation of NMDA receptors in these rats leads to a readily observable generalized motor seizure, characterized by an increase in motor activity followed by clonic-tonic movements of the forelimbs and hindlimbs, and the continued loss of righting ability. These seizures are not blocked by administration of a non-NMDA selective antagonist drug, but are readily blocked by NMDA selective compounds.

Animals were injected by the intraperitoneal route with the test drug (1 ml/100 g of body weight) and observed for a 30 minute period for seizure (potential agonist) activity. They were then injected with NMDA at a dose of 20 mg/kg body weight i.p. to test for antagonist activity. In control rats (normal saline administered) this dose of NMDA results in seizures in more than 95% of the animals. Rats were observed for seizures an additional 30 minute period following NMDA administration. Animals were rated as being positive or negative for the clear demonstration of tonic-clonic seizure activity with loss of righting ability. Observations of seizures induced by the test compound alone (agonist activity) or blockade of NMDA-induced seizures by the test compound (antagonist activity) were scored separately. Generally, five animals were used at each dose of compound. The entire range and intervals of the doses used was 200, 100, 50, 20, 10, 5, 2, and 1 mg/kg. Doses were decreased in a stepwise fashion in this range until at least 3 out of 5 animals exhibited seizures. The minimum effective dose (MED) was the lowest test dose which prevented NMDA-induced seizures in at least 3 out of 5 animals as reported in Table 11.

TABLE II

| Minimum Effective Dose of Compounds of Formula I Against Neonatal Rat Convulsions | |
|---|---|
| Compound of Example No. | MED (mg/kg) |
| 1 | 100 |
| 2 | 20 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| 4-[3-(1(2)H—tetrazol-5-yl)propyl]-2-piperazinecarboxylic acid | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below;

|  | Quantity (mg/tablet) |
|---|---|
| 4-[2-(1(2)H—tetrazol-5-yl)ethyl]-2-piperazinecarboxylic acid | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
|---|---|
| N—benzenesulfonyl-4-[2-(1(2)H—tetrazol-5-yl)ethyl]-2-piperazinecarboxamide | 0.25 |
| ethanol | 29.75 |
| Propellant 22 (chlorodifluoromethane) | 70.0 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets each containing 60 mg of active ingredient are made as follows:

| 5-(4-[3-(1(2)H—tetrazol-5-yl)propyl]-piperazin-2-yl)-1(2)H—tetrazole | 60 mg |
|---|---|
| starch | 45 mg |
| microcrystalline cellulose | 35 mg |
| polyvinylpyrrolidone | 4 mg |

-continued

| (as 10% solution in water) | |
|---|---|
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| 2,2-dimethylpropanoyloxymethyl 4-[3-(1(2)H—tetrazol-5-yl)propyl]-2-piperazinecarboxylate | 80 mg |
|---|---|
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

| N—methanesulfonyl-4-[3-(1(2)H—tetrazol-5-yl)propyl]-2-piperazinecarboxamide | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| n-Butyl 4-(2-[1(2)H—tetrazol-5-yl]ethyl)-2-piperazinecarboxylate | 50 mg |
|---|---|
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| | |
|---|---|
| 4-(3-[1(2)H—tetrazol-5-yl]propyl)-2-piperazinephosphonic acid | 100 mg |
| isotonic saline | 1000 ml |

The solution of the above ingredients is administered intravenously at a rate of 1 ml per minute to a subject in need of treatment.

I claim:

1. A compound of the formula

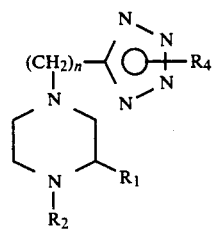
I wherein:
$R_1$ is

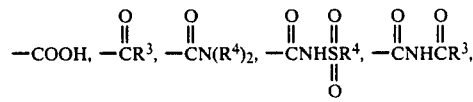

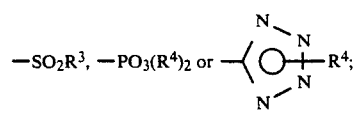

$R_2$ is hydrogen, $C_1-C_4$ alkyl, or phenyl-substituted $C_1-C_4$ alkyl;

M is 2 or 3;

each $R^3$ is independently $C_1-C_{16}$ alkoxy, phenyl-substituted $C_1-C_4$ alkoxy, or an oral ester forming group;

each $R^4$ is independently hydrogen, $C_1-C_{16}$ alkyl, phenyl-substituted $C_1-C_4$ alkyl, or phenyl; or a pharmaceutically acceptable salt thereof.

2. A compound of claim 1 wherein $R_1$ is —COOH.

3. A compound of claim 2 wherein $R_2$ is hydrogen.

4. A compound of claim 3 having the Formula Ia

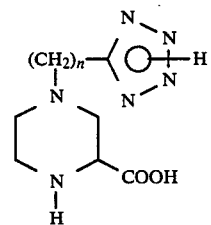
Ia or a pharmaceutically acceptable salt thereof.

5. The compound of claim 4 which is 4-[3-(1(2)H-tetrazol-5-yl)propyl]-2-piperazinecarboxylic acid or a pharmaceutically acceptable salt thereof.

6. The compound of claim 4 which is 4-[2-(1(2)H-tetrazol-5-yl)ethyl]-2-piperazinecarboxylic acid or a pharmaceutically acceptable salt thereof.

7. A method of blocking one or more excitatory amino acid receptors in mammals which comprises administering to a mammal requiring decreased excitatory amino acid neurotransmission a pharmaceutically effective amount of a compound of claim 1.

8. A method of treating epilepsy in mammals comprising administering to the mammal in need of treatment from epilepsy an antiepileptic amount of a compound of claim 1.

9. A method of treating stroke in mammals comprising administration to a mammal requiring treatment from a stroke an antistroke amount of a compound of claim 1.

10. A method of treating anxiety in mammals comprising administration to a mammal requiring treatment from anxiety an antianxiety amount of a compound of claim 1.

11. A method of treating cerebral ischaemia in mammals comprising administration to a mammal requiring treatment from cerebral ischaemia an antiischaemic amount of a compound of claim 1.

12. A method of treating muscular spasms in mammals comprising administration to a mammal requiring treatment from muscular spasms an antispasmodic amount of a compound of claim 1.

13. A method of treating Alzheimer's Disease in mammals comprising administration to a mammal requiring treatment from Alzheimer's Disease a pharmaceutically effective amount of a compound of claim 1.

14. A method of treating Huntington's Disease in mammals comprising administration to a mammal requiring treatment from Huntington's Disease a pharmaceutically effective amount of a compound of claim 1.

15. A pharmaceutical formulation comprising an effective amount of a compound of claim 1 and a pharmaceutically acceptable carrier, diluent or excipient therefor.

16. A pharmaceutical formulation comprising an effective amount of a compound of claim 4 and a pharmaceutically acceptable carrier, diluent or excipient therefor.

17. A formulation according to claim 16 wherein the compound is 4-[3-(1(2)H-tetrazol-5-yl)propyl]-2-piperazinecarboxylic acid or a pharmaceutically acceptable salt thereof.

18. A formulation according to claim 16 wherein the compound is 4-[2-(1(2)H-tetrazol-5-yl)ethyl -2-piperazinecarboxylic acid or a pharmaceutically acceptable salt thereof.

* * * * *

UNITED STATES PATENT AND TRADEMARK OFFICE
CERTIFICATE OF CORRECTION

PATENT NO. : 4,902,687

DATED : February 20, 1990

INVENTOR(S) : Paul L. Ornstein

It is certified that error appears in the above-identified patent and that said Letters Patent is hereby corrected as shown below:

In column 11, line 56 change "M" to read -- n --.

Signed and Sealed this

Thirtieth Day of June, 1992

*Attest:*

DOUGLAS B. COMER

*Attesting Officer*      *Acting Commissioner of Patents and Trademarks*